(12) United States Patent
Kitchen et al.

(10) Patent No.: US 6,376,706 B2
(45) Date of Patent: *Apr. 23, 2002

(54) CATALYST AND USE THEREOF IN THE PRODUCTION OF VINYL ACETATE

(75) Inventors: Simon James Kitchen, Hillam (GB); Daiyi Qin, Chengdu (CN)

(73) Assignee: BP Chemical Ltd., London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/315,938

(22) Filed: May 21, 1999

(30) Foreign Application Priority Data

May 22, 1998 (GB) .............................. 9810928

(51) Int. Cl.[7] .......................... C07C 67/00; C07C 67/05
(52) U.S. Cl. ........................ 560/241; 560/243; 560/245
(58) Field of Search ................. 502/305, 313, 502/314, 315, 317, 318, 319, 321, 322, 337, 344, 328, 325, 326, 327, 333, 335, 339, 340, 349, 350, 353

(56) References Cited

U.S. PATENT DOCUMENTS

| | | | |
|---|---|---|---|
| 3,373,189 A | | 3/1968 | Lum |
| 3,450,748 A | | 6/1969 | Schaeffer |
| 3,485,877 A | * | 12/1969 | Hargis et al. ............... 260/604 |
| 3,637,818 A | | 1/1972 | Krekeler et al. |
| 3,759,839 A | * | 9/1973 | Fernholtz et al. ........ 252/431 C |
| 3,903,139 A | * | 9/1975 | Fernholz et al. ............ 260/497 |
| 3,969,274 A | * | 7/1976 | Frampton ................... 252/456 |
| 3,970,697 A | | 7/1976 | Scheben et al. |
| 4,048,096 A | * | 9/1977 | Bissot ........................ 252/430 |
| 4,188,490 A | | 2/1980 | Hinnenkamp et al. |
| 4,356,316 A | | 10/1982 | Aoshima et al. |
| 5,185,308 A | | 2/1993 | Bartley et al. |
| 5,557,014 A | * | 9/1996 | Grate et al. ................. 568/401 |
| 5,576,457 A | * | 11/1996 | Abel .......................... 560/245 |
| 5,622,908 A | * | 4/1997 | Abel et al. .................. 502/339 |
| 5,672,734 A | * | 9/1997 | Abel et al. .................. 560/245 |
| 5,674,800 A | * | 10/1997 | Abel et al. .................. 502/326 |
| 5,777,715 A | * | 7/1998 | Abel et al. .................. 560/245 |
| 5,783,726 A | * | 7/1998 | Lemanski et al. .......... 560/261 |
| 5,972,824 A | * | 10/1999 | Herzog et al. .............. 502/160 |
| 5,998,659 A | * | 12/1999 | Abel .......................... 560/245 |
| 6,040,474 A | | 3/2000 | Jobson et al. |

FOREIGN PATENT DOCUMENTS

GB 1139210 1/1969

OTHER PUBLICATIONS

Abstract No. 68–74624P/00; "Preparation of unsaturated organic esters . . . ".
Abstract No. 80–14700C, "Ethylene catalytic oxidn. to mixt. of acetic acid . . . ".
Abstract No. 68–33014P/00, "Vinyl acetate prepn".
Abstract No. 1969:460745, "Vinyl acetate, acetaldehyde . . . ".
Abstract 52924R–AE, "Vinyl esters produced by oxidation of olefins . . . ".
Abstract 98–145537/13, "Integrated production of acetic acid and vinyl acetate . . . ".
Abstract 71–80846S, "Carboxylic acids prodn—by catalytic oxidation of olefins . . . ".
Abstract 94–318315/40, "Acetic acid prepn.—by reacting ethylene and . . . ".
Abstract 93–83805/10, "Catalyst for liq. phase–oxidn. of ethylene . . . ".

* cited by examiner

Primary Examiner—Steven P. Griffin
Assistant Examiner—Cam N. Nguyen
(74) Attorney, Agent, or Firm—Nixon & Vanderhye

(57) ABSTRACT

A catalyst for use in the production of vinyl acetate which comprises (1) a catalyst support, (2) palladium, (3) an acid, (4) at least one acetic acid catalyst promoter and (5) at least one vinyl acetate promoter and/or co-promoter. A process for the production of vinyl acetate from ethylene and an oxygen-containing gas using the catalyst.

23 Claims, No Drawings

CATALYST AND USE THEREOF IN THE PRODUCTION OF VINYL ACETATE

BACKGROUND OF THE INVENTION

The present invention relates to a process for the production of vinyl acetate and to a novel catalyst for use in the process.

Vinyl acetate is generally prepared commercially by contacting acetic acid and ethylene with molecular oxygen in the presence of a catalyst active for the production of vinyl acetate.

The catalyst suitable for use in the production of vinyl acetate may comprise a Group VIII metal, for example palladium, an alkali metal acetate promoter, for example sodium or potassium acetate, and an optional co-promoter, for example cadmium acetate or gold. In particular U.S. Pat. No. 5,185,308 discloses a process for preparing vinyl acetate by the catalytic oxidation of ethylene in the presence of acetic acid. The catalyst used is a supported palladium catalyst promoted with gold and potassium acetate.

Acetic acid, useful as a feedstock for the production of vinyl acetate, may be prepared by several methods as commonly practiced in the industry, for example by the liquid phase carbonylation of methanol and/or a reactive derivative thereof in the presence of a Group VIII noble metal catalyst, an alkyl iodide promoter and a finite concentration of water. The acetic acid produced is then used as a reactant in the production of vinyl acetate. The process, thus tends to be a two stage process.

U.S. Pat. No. 3,373,189 relates to a process for the production of vinyl acetate from ethylene and oxygen using a palladium catalyst. U.S. Pat. No. 4,188,490 discloses a process for the production of acetic acid and vinyl acetate using a palladium catalyst on a zinc oxide support. U.S. Pat. No. 3,637,818 discloses a process for the production of acetaldehyde, acetic acid and vinyl acetate by the oxidation of ethylene in the presence of a noble metal and manganese or cobalt oxides. The aforementioned processes are carried out in the liquid phase.

DESCRIPTION OF THE INVENTION

We have now found that vinyl acetate can be produced directly from a reactant mixture comprising ethylene, optionally water, and an oxygen-containing gas without the need to initially produce acetic acid as a separate stage in the overall process Through the use of a modified palladium catalyst, vinyl acetate can be produced directly in a one stage process.

Accordingly, the present invention provides a process for the production of vinyl acetate which comprises reacting ethylene with an oxygen-containing gas, and optionally water, in the presence of a catalyst comprising (1) a catalyst support, (2) palladium, (3) an acid, (4) at least one acetic acid catalyst promoter and (5) at least one vinyl acetate catalyst promoter and/or co-promoter.

In a further embodiment of the present invention there is provided a catalyst for use in the production of vinyl acetate which comprises (1) a catalyst support, (2) palladium, (3) an acid, (4) at least one acetic acid catalyst promoter and (5) at least one vinyl acetate catalyst promoter and/or co-promoter.

The present invention provides a novel and cost effective route for the production of vinyl acetate. The process is not only highly selective towards the production of vinyl acetate but does not require the independent and separate production of acetic acid which is then used as a co-reactant in the process. In contrast, use of the modified palladium catalyst results in the in-situ oxidation of the reactants to produce acetic acid which is then oxidised with ethylene to vinyl acetate. The bi-functional nature of the catalyst results in a direct process.

The present invention provides a process for the production of vinyl acetate from ethylene, an oxygen-containing gas and optionally water. The ethylene may be substantially pure or may be admixed with one or more of nitrogen, methane, ethane, carbon dioxide, hydrogen, and low levels of $C_3/C_4$ alkenes or alkanes.

The oxygen-containing gas may be air or a gas richer or poorer in molecular oxygen than air. Suitably, the gas may be oxygen diluted with a suitable diluent, for example nitrogen or carbon dioxide. Preferably, the oxygen-containing gas is oxygen.

Water may be optionally co-fed into the reaction chamber. Where water is present in the reaction chamber, it may be present in an amount up to 50 volume percent, preferably in the range from 10 to 30 volume percent.

A small amount of acetic acid may also be introduced into the reaction chamber. Suitably, the acetic acid may be introduced through a recycle stream. Where it is desired to introduce acetic acid, this may be present in an amount up to 50 volume percent, preferably in the range from 5 to 20 volume percent.

The catalyst of the present invention comprises palladium. The palladium concentration may be greater than 0.5% by weight, preferably greater than 1% by weight based upon the total weight of the catalyst. The palladium concentration may be as high as 10% by weight for fixed bed or fluid bed applications.

The catalyst of the present invention is a supported catalyst. Suitable catalyst supports may comprise porous silica, alumina, silica/alumina, titania, zirconia or carbon. Preferably, the support is silica. Suitably, the support may have a pore volume from 0.2 to 3.5 ml per gram of support, a surface area of 5 to 800 $m^2$ per gram of support and an apparent bulk density of 0.3 to 1.5 g/ml. For catalysts used in fixed bed processes, the support typically has dimensions of 3 to 9 mm and may be spheric, tablet, extrudate, pill shaped or any suitable shape. For catalysts used in fluid bed processes, the support typically may have a particle size distribution such that at least 60% of the catalyst particles have a particle diameter of below 200 microns, preferably at least 50% less than 105 microns and no more than 40% of the catalyst particles have a diameter of less than 40 microns.

The catalyst composition comprises at least one acetic acid catalyst promoter. Suitable promoters include selenium, titanium, tellurium and/or vanadium-containing compounds. Preferably, the acetic acid catalyst promoter is an oxide, acetate or acetylacetonate of at least one of the aforementioned metals. Preferably, the acetic acid catalyst promoter content of the final catalyst is up to 10% by weight.

In addition to the palladium compound and the acetic acid promoter, the catalyst comprises at least one vinyl acetate catalyst promoter and/or co-promoter, preferably both a promoter and a co-promoter. Suitable promoters include gold, copper and/or nickel, and cadmium acetate. A preferred promoter is gold. Suitable sources of gold include gold chloride, tetrachloroauric acid $HAuCl_4$, $NaAuCl_4$, $KAuCl_4$, dimethyl gold acetate, barium acetoaurate or gold acetate. The preferred gold compound is $HAuCl_4$. The metal may be present in an amount of from 0.1 to 10% by weight in the finished catalyst. Suitable co-promoters include alkali or alkaline earth metal salts, preferably an acetate salt, such as potassium or sodium acetate. Preferably, the co-promoter content in the final catalyst is in the range from 0.1 to 9.5% by weight as acetate. A preferred catalyst component (5) is gold and either sodium or potassium acetate.

The catalyst composition comprises an acid. Preferably, the acid is a strong acid. Suitable acids comprise heteropolyacids which may include silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadophosphoric acid, molybdovanadosilisic acid, borotungstic acid, boromolybdic acid, tungstomolybdoboric acid, molybdoaluminic acid, tungstoaluminic acid, molybdotungstoaluminic acid, molybdogermanic acid, tungstogermanic acid, molybdotungstogermanic acid, molybdotitanic acid, tungstotitanic acid, molybdotungstotitanic acid, cericmolybdic acid, cerictungstic acid, cericmolybdotungstic acid, molybdocobalt acid, tungstocobalt acid, molybdotungstocobalt acid, phosphoniobic acid, siliconiobic acid and silicotantalic acid. Among them, silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadosilisic acid, borotungstic acid, boromolybdic acid and boromolybdotungstic acid are especially preferred. Preferably, the acid content in the final catalyst is up to 50% by weight.

The final catalyst composition may suitably be optimised to maximise vinyl acetate production rate whilst maximising selectivity.

The catalyst of the present invention may suitably be prepared by the method described in detail in GB-A-1559540. In the first stage of the preparation process, the support is impregnated with a solution containing the required palladium and the promoter metal, for example gold, in the form of soluble salts. Example of such salts include the soluble halide derivatives. The impregnating solution is preferably an aqueous solution and the volume of solution used is such that it corresponds to between 50 and 100% of the pore volume of the support, preferably 95 to 99% of the pore volume for fixed bed catalysts or 50 to 99% of the pore volume for fluid bed catalysts.

After impregnation, the wet support is, optionally, treated with an aqueous solution of an alkali metal salt selected from alkali metal silicates, carbonates or hydroxides to develop a metal shell structure familiar to those skilled in the art. The amount of alkali metal salt used is such that after the solution has been in contact with the impregnated support for between 12 and 24 hours, the pH of the solution is suitably in the range 6.5 to 9.5, preferably 7.5 to 8 when measured at 25° C. The preferred metal salts are sodium metal silicate, sodium carbonate and sodium hydroxide.

During the treatment described above, palladium and promoter, for example gold, hydroxides are believed to be precipitated or incorporated onto the support. Alternatively, the impregnated support can be dried at ambient or reduced pressure and from ambient temperature to 150° C., preferably 60 to 120° C., prior to metals reduction. To convert such materials into the metallic state, the impregnated support is treated with a reducing agent such as ethylene, hydrazine, formaldehyde or hydrogen. If hydrogen is used, it will usually be necessary to heat the catalyst to 100 to 300° C. in order to effect complete reduction.

After the steps described above have been carried out, the reduced catalyst is washed with water and then dried. The dried carrier is then impregnated with the required amount of vinyl acetate catalyst co-promoter, for example aqueous alkali metal acetate, and acetic acid catalyst promoter, for example aqueous selenium-containing compound, and thereafter dried. The dried carrier is further treated with an appropriate amount of heteropoly acid dissolved in water, and the final product dried.

The method of catalyst preparation may be varied to optimise catalyst performance based on maximising vinyl acetate yield and selectivity.

Preparation of vinyl acetate using the catalyst of the present invention is typically carried out by contacting ethylene, water and an oxygen-containing gas such as oxygen or air with the catalyst at a temperature of from 100 to 400° C., preferably 140 to 210° C. and a pressure of 1 bar to 20 barg, preferably 6 to 15 barg.

The process may be carried out in a fixed bed or a fluidised bed reactor and is preferably carried out in the gas phase.

EXAMPLES

The present invention will now be illustrated with reference to the following Examples.

Example 1 is an example according to the present invention. Comparative Examples A, B and C are not according to the invention wherein the process utilised a catalyst not according to the present invention, Example A because it does not contain a vinyl acetate catalyst promoter or co-promoter, Example B because it does not contain an acid or an acetic acid catalyst promoter, and Example C because the acetic acid catalyst component and the vinyl acetate catalyst component are in separate beds.

Example 1

(a) Preparation of the Catalyst.

In an aqueous solution containing 1.7 g of sodium tetrachloropalladate (II) and 1.5 g of sodium tetrachloroaurate (III) hydrate dissolved in 34 g of water was placed 68.4 g of a porous silica carrie (KA 160 ex Sud Chemie) having a particle size 5 mm to 7 mm to absorb the entire solution. The resultant carrier was added to 76.5 g of an aqueous solution containing 6.5 g of sodium metasilicate and covered completely by the solution. The mixture was allowed to stand for 18 hours and then 20 g of 99% hydrazine hydrate was added to the solution to reduce Pd and Au. The resultant mixture was allowed to stand for 4 hours or until the reduction was complete. The carrier was separated from solution and washed with deionised water until no chloride ion was found in the effluent using a $AgNO_3$ solution. The resultant carrier was dried at 60° C. for 24 hours. In an aqueous solution containing 0.0071 g of potassium selenate (VI) and 0.51 g of potassium acetate dissolved in 5 g of water was added 10 g of the dried carrier. The carrier absorbed the entire solution and was dried at 60° C. for 24 hours. Thereafter, an aqueous solution containing 3.3 g of silicotungstic acid hydrate dissolved in 5 g water was added to the carrier and absorbed entirely. The resultant carrier containing Pd, Au, selenium salt and silicotungstic acid was dried at 60° C. for 24 hours.

Production of Vinyl Acetate 5 g of the resultant catalyst was distributed evenly in 60 mls glass beads (size 1 mm) in a reaction tube. A mixture of ethylene, oxygen, steam and inert gas in a volume ratio of 40:6:31:23 was introduced into the unit at a temperature of 160° C. and a pressure of 8 barg at a flow rate of 15.8 NL/hr to effect reaction. The effluent was analysed on line by gas chromatography. Vinyl acetate space time yield of 84.5 g/hr.L and selectivity of 76% was obtained based on carbon balance. $CO_2$ selectivity was 22%.

Comparative Example A
Preparation of Catalyst

Sodium tetrachloropalladate (II)(9.5 g) was dissolved in water (90 g). A porous silica carrier (KA 60 ex Sudchemie, particle size 5 mm to 7 mm) (180 g) was impregnated with this aqueous solution until the entire solution was absorbed. The resultant carrier was added to an aqueous solution (170 g) containing sodium metasilicate (17.7 g). The mixture as allowed to stand for 18 hours and then 20 g of 99% hydrazine hydrate was added to the solution to reduce the palladium. The resultant mixture was allowed to stand for 4 hours or until the reduction was complete. The carrier was separated from the solution and washed with de-ionised water until no chloride ion was found in the effluent using a AgNO3 solution. The resultant carrier was dried at 60° C. for 48 hours. Potassium selenate (VI) (0.164 g) was dissolved in water (10 g) and was absorbed entirely by 20 g of the dried carrier. Then the carrier was dried again at 60° C. for 24 hours. Thereafter, an aqueous solution containing silicotungstic acid hydrate (6.3) g dissolved in water (10 g) was added to the carrier and absorbed entirely. The resultant carrier containing palladium, selenium salt and silicotungstic acid was dried at 60° C. for 24 hours.

Five gram of the resultant catalyst was distributed evenly in 60 mls of glass beads (size 1 mm) in a reaction tube, a mixture of ethylene, oxygen, steam and an inert gas in a volume ratio of 40:6:31:23 was introduced into the unit at a temperature of 150° C. and a pressure of 8 bar G at a flow rate of 15.5 Nl/hr to effect reaction. The effluent was analysed on line by gas chromatography.

As a result the following data was obtained: acetic acid space time yield of 235 g/hr. 1, vinyl acetate space time yield of 2.1 g/hr. 1, acetaldehyde space time yield of 3.5 g/hr. 1 and carbon dioxide space time yield of 21.2 g/hr. 1. Overall selectivity to acetic acid was 87% and overall selectivity to vinyl acetate was 0.54%.

Comparative Example B
(a) Preparation of Catalyst

Vinyl acetate catalyst prepared according to U.S. Pat. No. 5,185,308 with nominal loadings of 0.9 Pd, 0.4 Au and 7 wt % KOAc on KA160.

Two and half gram of the resultant catalyst was distributed evenly in 60 mls of glass beads (size 1 mm) in a reaction tube, a mixture of ethylene, oxygen, steam and an inert gas in a volume ratio of 47:7:19:27 was introduced into the unit at a temperature of 150° C. and a pressure of 8 bar G at a flow rate of 21.1 Nl/hr to effect reaction. The effluent was analysed on line by gas chromatography.

As a result the following data was obtained carbon dioxide space time yield of 119.6 g/hr.1, no acetic acid, vinyl acetate or other by-products were detected.

Comparative Example C
(a) Preparation of Catalyst

Catalysts were prepared according to Comparative Examples A and B.

(b) Production of Vinyl Acetate

A reaction tube was packed with Catalyst 1 (5 g) and 2 (2.5 g) and glass beads (60 ml, size 1 mm). Catalyst 1 distributed evenly in glass beads (32 ml) was placed in the upper part of the tube and Catalyst 2 in glass beads (16 ml) at the lower. There were 2 ml glass beads between Catalyst 1 section and Catalyst 2, and 5 ml each at the top and the bottom of the tube. A mixture of ethylene, oxygen, steam and an inert gas in a volume ratio of 50:8:21:21 was introduced into the unit at a temperature of 150° C. and a pressure of 8 bar G at a flow rate of 15.8 Nl/hr to effect reaction. The effluent was analysed by on line gas chromatography.

The following results were obtained: vinyl acetate space time yield of 115 g/hr.1 with a selectivity of 77% based on carbon balance, CO2 selectivity of 11% and acetic acid selectivity of 5%. Ethyl acetate and ethanol were minor by-products.

It can be seen that reaction selectivities are only achieved which are comparable to those achieved from the claimed process when a two-stage process is operated.

We claim:

1. A process for the production of vinyl acetate which comprises reacting ethylene with an oxygen-containing gas in the presence of a catalyst comprising (1) a catalyst support, (2) palladium, (3) an acid, (4) at least one acetic catalyst promoter, and (5) at least one vinyl acetate promoter selected from the group consisting of cadmium acetate and metallic nickel.

2. A process as claimed in claim 1 in which the support comprises a member selected from the group consisting of porous silica, alumina, silica/alumina, titania, zirconia and carbon.

3. A process as claimed in claim 2 in which the acid is a strong acid selected from a heteropolyacid.

4. A process as claimed in claim 3 in which the acid content is up to 50% by weight.

5. A process as claimed in claim 2 in which the acetic acid catalyst promoter is selected from the group consisting of selenium, titanium, tellurium and vanadium-containing compounds.

6. A process as claimed in claim 5 in which the acetic acid catalyst promoter is an oxide, acetate or acetylacetonate.

7. A process as claimed in claim 1 in which the acid is a strong acid selected from a heteropolyacid.

8. A process as claimed in claim 7 in which the acid content is up to 50% by weight.

9. A process as claimed in claim 7 in which the acetic acid catalyst promoter is selected from the group consisting of selenium, titanium, tellurium and vanadium-containing compounds.

10. A process as claimed in claim 9 in which the acetic acid catalyst promoter is an oxide, acetate or acetylacetonate.

11. A process as claimed in claim 1 in which the acetic acid catalyst promoter is selected from the group consisting of selenium, titanium, tellurium and vanadium-containing compounds.

12. A process as claimed in claim 11 in which the acetic acid catalyst promoter is an oxide, acetate or acetylacetonate.

13. A process as claimed in claim 1 carried out at a temperature of from 100 to 400° C. and under a pressure of 1 to 20 barg.

14. A process as claimed in claim 1 in which the catalyst further comprises a vinyl acetate catalyst co-promoter.

15. A process as claimed in claim 14 in which the vinyl acetate catalyst co-promoter is selected from the group consisting of alkali and alkaline earth metal salts.

16. A process as claimed in claim 15 in which the vinyl acetate co-promoter is sodium acetate or potassium acetate.

17. A process as claimed in claim 1, wherein the reaction is carried out in the presence of co-fed water.

18. A process for the production of vinyl acetate which comprises reacting ethylene with an oxygen-containing gas in the presence of a catalyst which comprises (1) a catalyst support, (2) palladium, (3) and acid; (4) at least one acetic acid catalyst promoter selected from the group consisting of selenium, titanium, tellurium and vanadium-containing compounds, and (5) at least one vinyl acetate promoter selected from the group consisting of cadmium acetate and metallic nickel.

19. A process as claimed in claim 18, wherein the acid is a strong acid selected from a heteropolyacid.

20. A process as claimed in claim 18, wherein the reaction is carried out in the presence of co-fed water.

21. A process for the production of vinyl acetate which comprises reacting ethylene with an oxygen-containing gas in the presence of a catalyst which comprises (1) a catalyst support, (2) palladium, (3) an acid, (4) at least one acetic acid catalyst promoter selected from the group consisting of selenium, titanium, tellurium and vanadium-containing compounds, (5) at least one vinyl acetatae promoter selected from the group consisting of cadmium acetate and metallic nickel and 6) at least one vinyl acetate co-promoter.

22. A process as claimed in claim 21, wherein the acid is a strong acid selected from a heteropolyacid.

23. A process as claimed in claim 21, wherein the reaction is carried out in the process of co-fed water.

* * * * *